April 4, 1972 C. F. ZAIGER Plant Pat. 3,101
NECTARINE TREE
Filed July 24, 1969
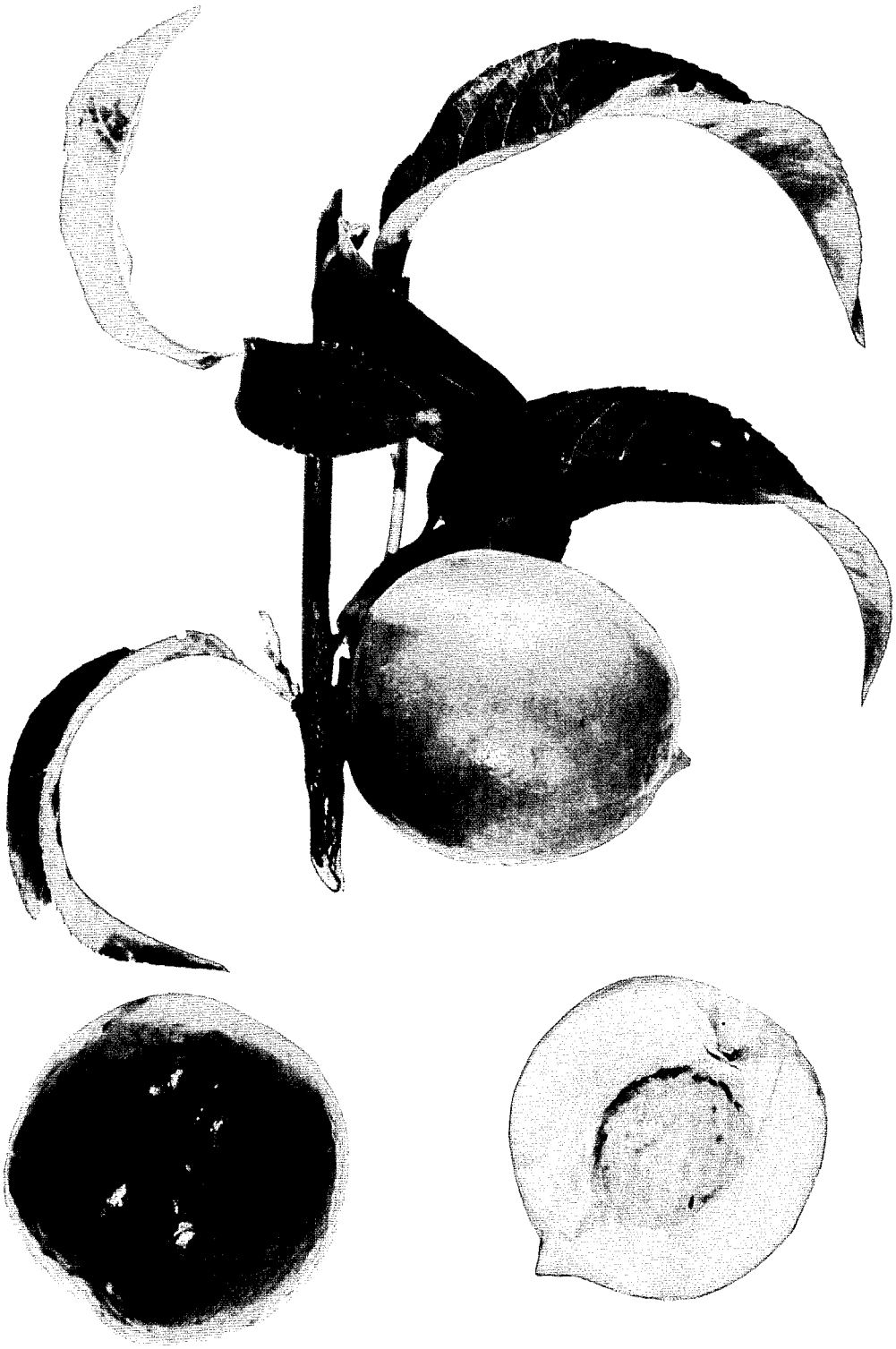
INVENTOR
C. Floyd Zaiger

United States Patent Office

Plant Pat. 3,101

Patented Apr. 4, 1972

3,101

NECTARINE TREE

Chris Floyd Zaiger, 537 Rosemore Ave., Modesto, Calif. 95351

Filed July 24, 1969, Ser. No. 844,673

Int. Cl. A01h 5/03

U.S. Cl. Plt.—41 1 Claim

This invention relates to a new and distinct variety of nectarine tree which bears large yellow-flesh, clingstone fruit characterized, as to novelty, by early ripening, the ripening period being approximately five days earlier than Grand River (Plant Patent #1248), having an exceptional high degree of shiny red color. The fruit is further characterized by being very firm, with excellent shipping and handling qualities. The high degree of large highly colored, firm fruits fills the needs of this early period for a high quality nectarine that will ship long distances.

The herein claimed variety of nectarine tree was originated by me in my experimental orchard located at Modesto, Calif., as a second generation seedling of a cross between the Sun Grand Nectarine (Plant Patent #974) and Late Le Grand (Plant Patent #1035).

Asexual propagation by budding and grafting of this new nectarine variety shows the subsequently described characteristics proved to be identical with the original nectarine tree.

The following is a detailed description of the foliage and fruit of my new variety, as based upon observations of specimens grown near Modesto, Calif., with color terminology in accordance with Reinhold Color Atlas by A. Kornerup and J. H. Wanscher.

Tree:
- *Size.*—Large.
- *Vigor.*—Vigorous.
- *Density.*—Dense.
- *Form.*—Spreading.
- *Productive.*—Very productive.
- *Bearing.*—Regular bearer.

Trunk:
- *Size.*—Stocky to medium.
- *Surface.*—Medium shaggy.
- *Color.*—Brownish gray.

Branches:
- *Size.*—Medium stocky.
- *Surface.*—Medium shaggy.
- *Color.*—Brown to grayish brown.
- *Lenticels.*—Medium quantity.

Leaves:
- *Size.*—Large to medium. Average length 6½". Average width 1¼".
- *Texture.*—Smooth.
- *Margin.*—Crenate.
- *Petiole.*—Medium length.
- *Glands.*—Usually two or more, medium size, reniform.
- *Color.*—Upper surface medium green (27E7), lower surface lighter green (28D8), heavy midrib on lower surface yellow green (30B6).

Flower buds:
- *Size.*—Large.
- *Length.*—Medium.
- *Form.*—Plump.

Flowers:
- *Blooming period.*—Date of first bloom Mar. 7, 1965. Date of full bloom Mar. 13, 1965.
- *Size.*—Large.

- *Pollen.*—Present.
- *Color.*—Pink.

Fruit:
- *Maturity when described.*—June 13, 1965.
- *Date of first picking.*—June 6, 1965.
- *Date of last picking.*—June 13, 1965.
- *Size.*—Uniform, large to medium. Average diameter axially 2¾". Average transversely in suture plane—2½".
- *Form.*—Symmetrical; narrowly ovoid.
- *Suture.*—Shallow, extends from base to apex.
- *Ventral surface.*—Rounded slightly, lips mostly equal.
- *Cavity.*—Rounded, average depth ⅜".
- *Apex.*—Moderately prolonged.

Skin:
- *Thickness.*—Thick to medium.
- *Texture.*—Smooth to medium smooth, tenacious to flesh.
- *Tendency to crack.*—None.
- *Down.*—Wanting.
- *Color.*—Red (10B8 to 10D8). Yellow under color (4B8).

Flesh:
- *Juice.*—Moderate.
- *Amygadalin.*—Moderate.
- *Texture.*—Medium, meaty.
- *Fibers.*—Few, fine, tender.
- *Ripens.*—Comparatively even.
- *Flavor.*—Subacid.
- *Eating quality.*—Good.
- *Color.*—Yellow (4B8 shading to 3B7).

Stone:
- *Type.*—Clingstone.
- *Size.*—Medium, average length, average breadth, average thickness.
- *Form.*—Ovoid.
- *Base.*—Straight to slightly oblique.
- *Apex.*—Acute.
- *Sides.*—Equal.
- *Surface.*—Pitted throughout.
- *Ridges.*—Rounded.
- *Pits.*—Angular.
- *Dorsal edge.*—Full, with broad groove to above center.
- *Tendency to split.*—Slight.
- *Color.*—Light brown (8C4).

Use: Market; dessert.

Keeping quality: Very good.

Shipping quality: Very good.

The tree and its fruit herein described may vary in slight detail due to climatic and soil conditions under which this variety may be grown; the present description being of the variety grown in Modesto, Calif.

The following is claimed:

1. A new and distinct variety of nectarine tree, as illustrated and described, which bears large to medium clingstone fruit having yellow flesh approximately five days earlier than Grand River (Plant Patent #1248), but being an improvement by bearing larger, firmer fruits than other nectarines at this maturity period and further characterized by having a very high degree of red color over nearly the entire exterior area of the fruit.

No references cited.

ROBERT E. BAGWILL, Primary Examiner